US007867985B2

(12) United States Patent
Burdick et al.

(10) Patent No.: US 7,867,985 B2
(45) Date of Patent: Jan. 11, 2011

(54) BIOLOGICAL LUBRICANT COMPOSITION AND METHOD OF APPLYING LUBRICANT COMPOSITION

(75) Inventors: Julie-Anne Mason Burdick, Gilbert, AZ (US); Martine Laberge, Seneca, SC (US); Gary Lickfield, Easley, SC (US)

(73) Assignee: Clemson University Research Foundation, Clemson, SC (US)

( * ) Notice: Subject to any disclaimer, the term of this patent is extended or adjusted under 35 U.S.C. 154(b) by 1862 days.

(21) Appl. No.: 10/853,611

(22) Filed: May 25, 2004

(65) Prior Publication Data

US 2005/0164981 A1 Jul. 28, 2005

Related U.S. Application Data

(62) Division of application No. 09/569,009, filed on May 11, 2000, now Pat. No. 6,800,298.

(51) Int. Cl.
*A61K 31/721* (2006.01)
*C08B 37/02* (2006.01)
(52) U.S. Cl. ........................... 514/59; 536/112
(58) Field of Classification Search ................. 424/489; 514/54
See application file for complete search history.

(56) References Cited

U.S. PATENT DOCUMENTS

| 5,238,929 | A | 8/1993 | Koupchinov et al. |
| 5,614,515 | A | 3/1997 | Rodgers et al. |
| 5,625,036 | A | 4/1997 | Hawkins et al. |
| 5,866,570 | A | 2/1999 | Liang et al. |
| 5,874,500 | A | 2/1999 | Rhee et al. |
| 5,902,800 | A | 5/1999 | Green et al. |
| 5,906,934 | A | 5/1999 | Grande et al. |
| 5,912,270 | A | 6/1999 | Dixon et al. |
| 5,939,323 | A | 8/1999 | Valentini et al. |
| 5,980,887 | A | 11/1999 | Isner et al. |
| 5,985,330 | A | 11/1999 | Collin |
| 6,475,516 | B2 | 11/2002 | DiCosmo et al. |

FOREIGN PATENT DOCUMENTS

| EP | 0499164 | * | 8/1992 |
| EP | 0499164 | A1 | 8/1992 |
| EP | 0810239 | A2 | 3/1997 |
| EP | 0767212 | A1 | 4/1997 |
| WO | WO 8901777 | | 3/1989 |
| WO | WO 9534287 | | 12/1995 |
| WO | WO 9615795 | A1 | 5/1996 |
| WO | WO97/22345 | * | 6/1997 |
| WO | WO 9722345 | | 6/1997 |
| WO | WO98/00170 | * | 1/1998 |
| WO | WO 9800170 | | 1/1998 |

OTHER PUBLICATIONS

Article—*Double-stimuli-responsive degradation of hydrogels consisting of oligopeptide-terminated poly(ethylene glycol) and dextran with an interpenetrating polymer network*, Motoichi Kurisawa, Minoru Terano, and Nobuhiko Yui, J. Biomater. Sci. Polymer Edn. vol. 8, No. 9, 1997, pp. 691-708.
Article—*Bioerodible Hydrogels Based on Photopolymerized Poly-(ethylene glycol)-co-poly(α-hydroxy acid) Diacrylate Macromer* Amarpreet S. Sawhney, Chandrashekhar P. Pathak, and Jeffrey A. Hubbel, Macromolecules, vol. 26, No. 4, 1993, pp. 581-587s.
Article—*Biodegradation* in vitro *and retention in the rabbit eye of crosslinked poly(1-vinyl-2-pyrrolidinone) hydrogel as a vitreous substitute*, Ye Hong, Traian V. Chirila, Sarojini Vijayasekaran, Weiyong Shen, Xia Lou, and Paul D. Dalton, J. Biomed. Mater. Res., vol. 39, 1998, pp. 650-659.
Thesis presented to the Graduate School of Clemson University entitled "A Polysaccharide Hydrogel As an Organic Carrier" by Julie-Anne Mason Burdick and released to Cooper Library, Clemson University, Aug. 16, 2001, pp. 1-69.
Hong et al., "Biodegradation in vitro and retention in the rabbit eye of crosslinked poly(1-vinyl-2-pyrrolidinone) hydrogel as a vitreous substitute", pp. 650-659, 1998.
Kito et al., "Biocompatible coatings for luminal and outer surfaces of small-caliber artificial grafts", pp. 321-330, Journal of Biomedical Materials Research, vol. 30, 1996.
Heller et al., "Development of enzymatically degradable protective coatings for use in triggered drug delivery systems: derivatized starch hydrogels", pp. 345-350. Biomaterials vol. 11, Jul. 1990.
Ocular Surgery News, "Biocompatibility increases comfort of new daily-wear soft contact lenses", pp. 1-2. http://www.slackinc.com/eye/osn/19967a/bio.htm, Jul. 1, 1996.
Cooke et al., "The rheology of synovial fluid and some potential synthetic lubricants for degenerate synovial joints", pp. 66-72. Engineering in Medicine, vol. 7, No. 2, 1978.
Gavrjushenko, "Recommendations with respect to the improvement of lubricating qualities of synovial fluid in artificial joints", pp. 111-114. Part H: Hornal of Engineering in Medicine, Proc Instn Mech Engrs vol. 207, 1993.
Mow et al., "Lubrication and Wear of Diarthrodial Joints", pp. 275-315. Lippincott-Raven Publishers, Philadelphia 1997.
Pruzanski et al., "Enzymatic Activity and Distribution of Phospholipase $A_2$ in Human Cartilage", pp. 2457-2459. Life Sciences, vol. 48, No. 25, 1991.

(Continued)

*Primary Examiner*—Eric S Olson
(74) *Attorney, Agent, or Firm*—Dority & Manning, P.A.

(57) ABSTRACT

Fluid compositions and methods for lubrication of mammalian joints are disclosed, including both natural and artificial fluids. Synovial fluid acts to lubricate the bearing surfaces of bones and bone-like structures which are held in frictional contact within biological joints. Such fluids may be used to treat arthritic, injured, and diseased joints. Synovial fluid containing a dextran-based hydrogel with lipids provides enhanced rheological and tribological properties of such a fluid. Phospholipids are particularly useful in dextran-based compositions for synovial fluid. One phospholipid that can be used advantageously in synovial fluid is dipalmitoyl phosphatidylcholine (DPPC).

16 Claims, 1 Drawing Sheet

OTHER PUBLICATIONS

Williams III et al., "Sliding friction analysis of phosphatidylcholine as a boundary lubricant for articular cartilage". Part H: Jornal of Engineering in Medicine, vol. 207, 1993.

Williams III et al., "Evaluation of the frictional properties of an elastomer with enhanced lipid-adsorbing ability", pp. 359-368. Proc Instn Mech Engrs vol. 211, Part H, 1997.

"Collaborative Biomedical Products" Product Specification Sheet, MATRIGEL Basement Membrane Matrix. Becton Dicksinson Labware, Bedford, MA 01730, Dec. 1997.

Hills, Brian A., "Oligalameller Lubrication of Joints by Surface Active Phospholipid", pp. 82-91, The Journal of Rheumatology, 1989.

Nangia, et al., "Analysis of preparation of dextran hydrogel membranes as a wound dressing", Drug Development and Industrial Pharmacy, 1991, vol. 17, No. 12, pp. 1609-1624.

John Wiley & Sons, Inc., Biodegradation in vitro and retention in the rabbit eye of crosslinked poly(1-vinyl-2-pyrrolidionon) hydrogel as a vitreous substitute, 1998.

Journal of Biomedical Materials Research, vol. 15, 591-603, (1981), Biodegradation of a poly-($\alpha$-amino acid) hydrogel.

Butterworth Heinemann Biomaterials 16 (1995) 441-447, Degradation of polydispersed poly(L-lactic acid) to modulate lactic acid release, Great Britain.

Elsevier Biomaterials 18 (1997), In vitro degradation of pH-sensitive hydrogels containing aromatic azo bonds, Great Britain.

Butterworth-Heinemann Biomaterials 1994, vol. 15 No. 11, 920-925, Molecular weight dependence of calcification of polyethylene glycol hydrogels.

ASAIO Journal 1993 M326-M331, Newly Designed Tissue Adhesion Prevention Technology Based on Photocurable Mucopolysaccharides, Japan.

Journal of Biomedical Materials Research, vol. 30, 321-330 (1996), Biocompatible coatings for luminal and outer surfaces of small-caliber artificial grafts.

Butterworth, Heinemann Biomaterials 1990, vol. 11 July, Development of enzymatically degradable protective coatings for use in triggered drug delivery systems: derivatized starch hydrogels.

American Chemical Society, Bioconjugate Chem. 1997, 8, 686-694, Synthesis and in Vitro Degradation of New Polyvalent Hydrazide Cross-linked Hydrogels of Hyaluronic Acid.

Department of Orthopaedic Surgery, University Hospital of Copenhagen, Blegdamsvej 9, 2100 Copenhagen, Denmark, Pathological Human Synovial FluidsDepartment of Pharmaceutics, Macromolecules 1995, 28, 6317-6322, Synthesis, Characterization, and Polymerization of Glycidyl Methacrylate Derivatized Dextran.

Polytechnic Institute of Jassy, Jassy, Romania, Polymeric Biomaterials, 1993.

Phospholipase $A_2$ in Human Cartlage, vol. 48 25, 1991, Table 2, Enzymatic Hydrolysis of 1-Palmitoyl-2-($^{14}$C)-Palmitoyl-3-Phosphatidylcholine.

Biocompatibility increases co . . . new daily-wear soft contact lenses, http://www.slackinc.com/eye/osn/19967a/bio.htm, Ocular Surgery News, 1996.

Journal of Biomedical Materials Research, vol. 29, 421-429 (1995), Wettability and interfacial interactions in bioceramic-body-liquid systems.

The Journal of Rheumatology 1993, vol. 20, Supplement 39, Viscosupplementation: A New Concept in the Treatment of Osteoarthritis.

Elsevier Science Publishers, Biochimica et Biophysica Acta 920 (1987) 301-305, Compound 48 / 80 is a potent inhibitor of phospholipase C and a dual modulator of phospholipase $A_2$ from human platelet.

Tropical Products Institute, Med. & Biol. Engng. vol. 7, pp. 507-516, Pergamon Press, 1969, Great Britain, The Rheological Behaviour of Synovial Fluid and Its Possible Relation to Joint Lubrication.

C&EN 970609-Intelligent Gels, Chemical & Engineering News, Jun. 9, 1997.

Annals of Internal Medicine, vol. 88, No. 6, Jun. 1978, Articular Damage in Arthritis and Its Control.

Inflammatory Diseases, Wyeth-Ayerst Research, Princeton, J.J., USA, Original Research Article, Cellular and Topical in vitro Inflammatory Murine Models in the Evaluation of Inhibitors of Phospholipase $A_2$, Skin Pharmacol 1995, 300-308Annals.

Annals of the Rheumatic Diseases, 1978, 37, 24-29, Altered phospholipids in human rheumatoid synoviocytes.

Part H: Journal of Engineering in Medicine, vol. 207, pp. 111-114, Recommendations with respect to the improvement of lubricating qualities of synovial fluid in artificial joints, Published 1993.

Annals of Biomedical Engineering, vol. 23, pp. 112-115, 1995, Remarkable Anti-Wear Properties of Joint Surfactant.

Annals of the Rheumatic Diseases, 1984, 43, 641-648, Surfactants identified in synovial fluid and their ability to act as boundary lubricants.

British Journal of Rheumatology 1998, 37, 143-147, Deficiency of Lubricating Lining the Articular Surfaces of Replaced Hips and Knees.

Agents and Actions, vol. 34, ½ (1991), 278-281, Interleukin-1 and synovial protein kinase C: Identification of a novel, 35 kDa cytosolic substrate.

Agents and Actions, vol. 34 ½ (1991), 106-109, vol. 27, ¾ (1989, 476-481, Phosphonate-phospholipid analogues inhibit human phospholipase $A_2$.

AJVR, vol. 58, No. 10, Oct. 1997, Effects of intravenous administration of sodium hyaluronate on carpal joints in exercising horses after arthroscopic surgery and osteochondral fragmentation.

British Society for Rheumatology 1998, 37, 137-142, Enzymatic Identification of the Load-Bearing Boundary Lubricant in the Joint.

Abstract published in Advance ACS Abstracts, Jul. 15, 1997, Macromolecules 1997, 30, 4639-4645, Degradation and Release Behavior of Dextran-Based Hydrogel.

Lippincott-Raven Publishers, Philadelphia, 1997, pp. 275-315, Basic Orthopaedic Biomechanics, 2nd ed., Lubrication and Wear of Diarthrodial Joints.

Journal of Orthopaedic Research 9, 341-347 Raven Press, Ltd., New York 1991, Effect of Extracellular Fatty Acids on Lipid Metabolism in Cultured Rabbit Articular Chondrocytes.

RMS-800/RDS-II Owner's Manual, 1990, Parallel Plate.

Journal of Lipid Mediators Cell Signalling 10 (1994) 315-330, Biochemical and pharmacological comparison of a cytosolic, high molecular weight phospholipase $A_2$, human synovial fluid phospholipase $A_2$ and CoA-independent transacylase.

Proc. Instn. Mech. Engrs. vol. 207, Sliding friction analysis of phosphatidylcholine as a boundary lubricant for articular cartilage, Published 1993.

Proc. Instn. Mech. Engrs. vol. 211 Part H, Evaluation of the frictional properties of an elastomer with enhanced lipid-adsorbing ability, Published 1997.

Nucl. Med. Biol. vol. 15 No. 2, pp. 151-156, 1988, Use of Liposomes as Carriers for Radiation Synovectomy.

Rheologica Acta, Band 5, Heft 1 (1966), A Rheological Measurement of Three Synovial Fluids.

J.M.S.—Pure Appl. Chem., A33(9), pp. 1249-1262 (1996, Rheology of Synovial Fluids and Substitute Polymers.

NCBI PubMed Query, J Drug Target 1995; 3(3), 209-16, The delivery of insulin from aqueous and non-aqueous reservoirs governed by a glucose sensitive gel membrane.

J. Physiol. 1953 119, 244-252, The Physiological Function of Hyaluronic Acid in Synovial Fluid; Viscous, Elastic and Lubricant Properties.

Artificial Organs 15(5), 414-419, Raven Press, Ltd., New York 1991, Biochemical Changes in Knee Joint Articular Cartilage After Cemented Prosthetic Hip Hemiarthroplasty in Dogs.

The Journal of Rheumatology 1993, vol. 20, Supplement 39, Intraarticular Hyaluronan Injections in the Treatment of Osteoarthritis: State of the Art Review.

Annals of the Rheumatic Diseases, 1979, 37, 553-557, Liposome-incorporated corticosteroids. II. Therapeutic activity in experimental aarthritis.

American Chemical Society 1994, 37, 337-341, Rational Modification of Human Synovial Fluid Phospholipase $A_2$ Inhibitors.

Life Sciences, vol. 48, pp. 2457-2462, Enzymatic Activity and Distribution of Phospholipase $A_2$ in Human Cartilage, Published 1991.

Clinical Orthopaedics and Related Research, No. 119, Sep. 1976, 237-241, Pathological Human Synovial Fluids.

Analytical Biochemistry 204, 190-197 (1992), Analysis of Human Synovial Fluid Phospholipase $A_2$ on Short Chain Phosphatidylcholine-Mixed Micelles: Development of a Spectrophotometric Assay Suitable for a Microtiterplate Reader[1].

Elsevier Science S.A. Wear 207 (1997) 86-91, Phospholipids as boundary lubricants in wear tests of prosthetic joint materials.

Am. J. Vet Res, vol. to, No. 12, Dec. 1989, Concentration and degree of polymerization of hyaluronate in equine synovial fluid.

Proc Instn Mech Engrs vol. 212 Part H, Adaptive multimode lubrication in natural synovial joints and artificial joints, Published 1998.

Nature, vol. 352, Jul. 4, 1991, Structure of recombinant human rheumatoid arthritic synovial fluid phospholipase $A_2$ at 2.2 A resolution.

J. Med. Chem. 1994, 37, 4118-4129, Substrate Specificity in Short-Chain Phospholipid Analogs at the Active Site Human Synovial Phospholipase $A_2$.

* cited by examiner

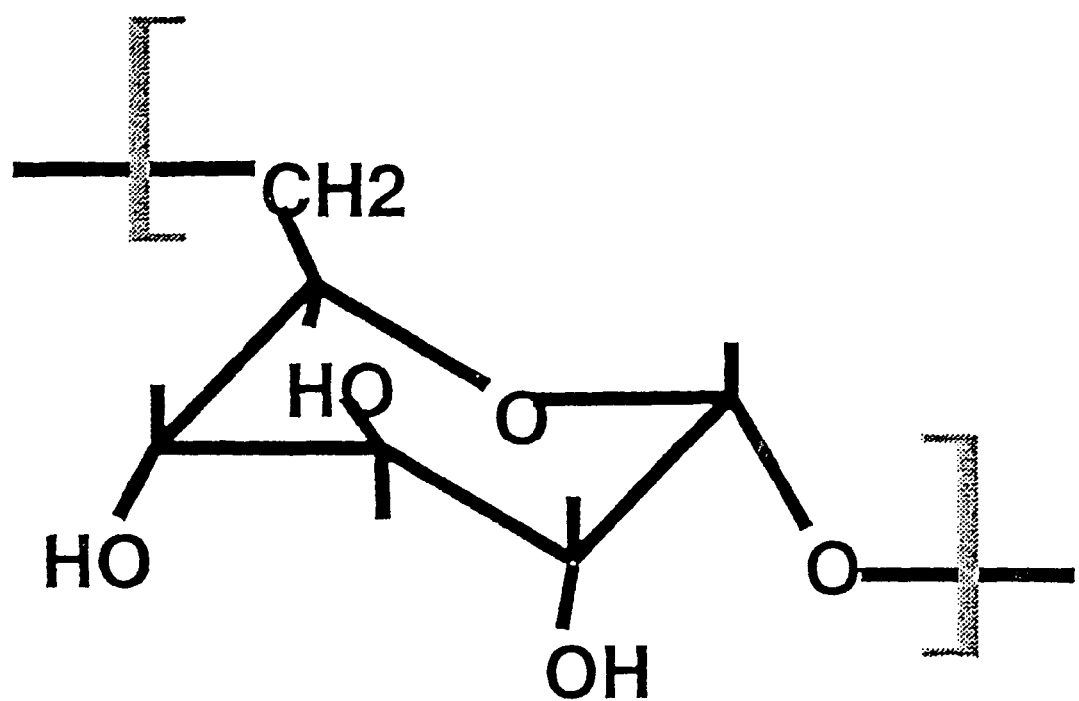
Figure 1 Chemical Structure of Dextran

BIOLOGICAL LUBRICANT COMPOSITION AND METHOD OF APPLYING LUBRICANT COMPOSITION

CROSS REFERENCE TO RELATED APPLICATION

This application is a divisional application of U.S. Application Ser. No. 09/569,009 having a filing date of May 11, 2000 now U.S. Pat. No. 6,800,298.

FIELD OF THE INVENTION

This invention relates to compositions, methods and apparatus for lubrication of mammalian joints, both natural and artificial.

BACKGROUND OF THE INVENTION

Synovial fluid acts to lubricate the bearing surfaces of bones and bone-like structures which are held in frictional contact within joints. Synovial fluid lubricates muscles, tendons, cartilage, bones, ligaments, and other biological structures that move within the body relative to each other. The human knee is an example of a joint that uses synovial fluid advantageously to provide for lubrication and friction reduction. Synovial fluid is naturally excreted into the cavity of the joint in a normal healthy knee.

There are publications disclosing the use of propylene glycol and phospholipids in synovial fluid. For example, PCT publication WO 97/22345 to Hills et al. provides a discussion of a method of lubrication of synovial fluid by administering a composition comprising a mixture of phospholipids and propylene glycol. Another publication, PCT publication 89/01777 discloses using phospholipids such as hyaluronic acid in saline solution as a lubricant for joints. Hyaluronic acid compositions may reduce the coefficient of kinetic friction between surfaces in contact with each other, and in particular, load bearing surfaces.

Another publication, EP 0 767 212A1, is directed to a process for producing an aqueous solution of phosphorycholine group bearing polymer. This publication is directed to producing such compositions as starting materials for cosmetics having skin beautifying effects, and as contact lens cleaning agents.

U.S. Pat. No. 5,902,800 to Green et al. describes pharmaceutical compositions containing dextran, and a method for treatment of joint inflammation and pain brought about by arthritis, physical trauma, or infection using such dextran-containing formulations. The method comprises administering a bimodal molecular weight dextran formulation in conjunction with drugs or pharmaceuticals, such as corticocosteroids, anti-inflammatory drugs, and antibiotics to enhance the effect of dextran in relieving pain and inflammation in an inflamed joint.

SUMMARY OF THE INVENTION

The present invention may be presented in many different embodiments, and representative embodiments are described herein. The invention is not limited to only those embodiments described, and a person of skill in the art may readily apply the invention in other ways that are apparent from this specification. Numerous examples are provided, but the invention is not intended to be limited to only those examples provided.

The invention generally comprises a biologically compatible lubricant composition useful for: injecting into damaged or diseased joints, filling cavities and spaces in artificial joints, applying to joints in connection with post-surgical procedures, and other applications in which a synovial fluid having good lubricity and biocompatibility is desirable. Treatment of osteo-arthritic joints is one application for compositions of this invention. In other applications, a composition may be injected following a joint injury, as a visco-supplementation. The compositions may be used as lubricants in artificial joints following total joint replacements. Further, the compositions may be used for maintenance of an artificial joint to minimize wear of bearing surfaces in humans or mammals. In some applications, the compositions may be used to investigate or measure the wear performance of artificial joints in vitro in a joint stimulator for research purposes.

The composition generally comprises an effective amount of dextran and a lipid. In one aspect of the invention, the lipid may be selected from the group of lipids comprising: lipopolysaccharides, sphingolipids, glycolipids, phosphatidyl cholines, phosphatidyl ethanolamines, sphingomyelins, phosphatidyl inositols, phosphatidyl serines, phosphatidylethanolamine, phosphatidylserine, phosphatidylglycerol, phosphatidylinositol, sphingomyelin, dipalmitoyl phosphatidylcholine (DPPC), and phosphatidyl cholines.

In one embodiment of the invention, the composition is presented which has a rheology of the fluid between about 1 and 20 Pa (sec) at a temperature range of about 25-45° C. The dextran typically comprises than 40% by weight of the solution, and more preferably about 20% by weight, and still more preferably about 10% by weight or less.

In another aspect of the invention, a synthetic synovial fluid is disclosed comprising dextran and a phospholipid. In many instances the fluid comprises a crosslinked hydrogel. Many different phospholipids work well in this composition, and one desirable phospholipid is dipalmitoyl phosphatidylcholine (DPPC), which is further discussed in connection with the Example below.

A method of lubricating a joint or other physiological articulation is also presented by way of this invention. The method generally comprises administering to a joint or articulation in an effective amount of a composition comprising one or more phospholipids and dextran-based hydrogel which acts as a carrier. The method may be applied in instances for which the joint is a natural joint, or an artificial joint. In one application, the method may be applied in which the administration of the composition follows a total joint replacement operation. In one aspect of the invention, the method may include applying the lubricant compositions into an artificial joint to simulate wear performance of the lubricant in a joint.

BRIEF DESCRIPTION OF THE DRAWING

The invention may be better understood by reference to the following drawing:

FIG. 1 shows a simplified schematic of dextran, which is used in the compositions of the invention.

DETAILED DESCRIPTION OF THE INVENTION

Reference now will be made to the embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention, which broader aspects are embodied in the exemplary constructions.

In one aspect of this invention, a hydrogel made from polysaccharides is employed to serve as a carrier for phospholipids, which are organic molecules found naturally in synovial joints such as the shoulder and knee. Phospholipids contribute to the lubricating properties of articular cartilage provided by the synovial fluid in normal joints.

Hydrogels are polymers that swell when exposed to water. Some hydrogels are made from dextran, a polysaccharide that has been used in the prior art as a plasma expander and a drug carrier. To fabricate the gels of this invention, dextran may be coupled with glycidyl methacrylate. Gelation may occur using an initiator system of ammonium peroxydisulfate and N,N,N',N'-tetramethyl-ethylene diamine.

Natural joint lubrication is a complex process that allows the joint to operate in different conditions. Such conditions include: joint surface velocity and load applied on the joint. At high loads and low velocity, boundary lubrication is used as a means to protect the surfaces and minimize their contact (this is termed boundary lubrication). At higher velocities, a fluid film is generated between the surfaces because of pressure build-up, and completely separates the surfaces. This is termed fluid film lubrication. Since cartilage is highly deformable under pressure, this deformation may enhance the thickness of the fluid film. This process is sometimes termed an elastohydrodynamic lubrication mechanism. Articular cartilage is filled with "water" that is squeezed from the surface upon loading.

Synovial fluid in the joint is necessary for effective levels of fluid film lubrication which is the primary lubrication mechanism at high speeds. In conditions of low speed, high load and rest, this mechanism is assisted by boundary lubrication achieved in a layer of molecules attached to the surface of the cartilage, also known as surfactant. These molecules act as a protective layer for the cartilage surfaces and basically provide the final line of defense against destructive contact and possibly wear of the articular cartilage.

The different types of phospholipid adsorbed onto the surface of cartilage have been isolated by extraction and identified by chromatography on silica gel paper and mass spectroscopy. The primary phospholipid classes identified have been quantified by a phosphate assay. Gas chromatography and electrospray ionization mass spectrometry are sometimes used to further characterize the fatty acyl chains in each major phospholipid component and to identify the molecular species present. Phosphatidylcholine (41%), phosphatidylethanolamine (27%) and sphingomyelin (32%) comprise the major components of the lipid layer on a normal cartilage surface. When present in a carrier such as Dextran, the phospholipid molecules (single phospholipid or a mixture of phospholipids) are released and are present in the synovial cavity available for boundary lubrication (or surfactant).

Lipid-containing polysaccharide hydrogels made from dextran and phospholipids may be successfully deployed in joints. Hydrogel containing lipids with a lesser degree of cross-linking provides better lubrication properties than hydrogels with more cross-linking, or hydrogels with no lipids at all.

Polysaccharide hydrogels can be organic carriers for entrapped phospholipids. A potential use for the hydrogels containing lipids could be as a replacement lubricant in synovial joints, including degenerated and artificial joints.

People who suffer from the pain and loss of mobility due to diseased joints may benefit from implants designed to improve their situation. Orthopedic implants made from natural polymers and incorporating beneficial ingredients from synovial fluid may alleviate the decreased motion in these joints. Biocompatibility of a material is one of the primary concerns for a successful implant. Degradable polymeric implants have advantages over non-degradable implants provided the material functions in a predictable manner and matches the properties of the tissue which it was designed to replace. For example, degradable polymers do not require removal. They also can provide temporary functions until the native tissue repairs itself. The degradation of polymeric implants can be regulated to be faster or slower, depending on the material of construction and the required functional properties. Lastly, using naturally occurring materials minimizes the body=s reaction to these implants.

Hydrogels

Hydrogels are water-swollen polymers made from natural or synthetic materials. They are made from monomers either by chemical reaction using a cross-linking agent, or by exposure to radiation such as electron beams, gamma radiation, X-rays, and ultraviolet light. The cross-linking forces that hold hydrogels together include: ionic interactions, hydrogen bonding, hydrophobic interactions, and van der Waals forces. The water content of the gel provides these materials their advantageous mechanical and surface properties. Further, it sometimes dictates their interaction with biological surfaces.

Generally, hydrogels degrade by two main mechanisms: physical (e.g., fracture) or chemical (e.g., hydrolysis, enzymatically). Several factors contribute to the rate of their degradation including the chemical composition, degree of swelling, the presence of enzymes, pH, and temperature. The degradation of hydrogels is mostly controlled by the degree of swelling which is determined by hydrophilicity and degree of cross-linking.

Degradation of Hydrogels

Hydrogels have been studied for their potential for controlled degradation. A synthetic synovial fluid must degrade at an acceptable rate to effectively serve as a carrier. Co-polymers, especially, have been formulated to control the rate of degradation. Some researchers have produced interpenetrating network polymers from polyethylene glycol (PEG) and dextran. These researchers have studied the in vitro degradation of the PEG/dextran hydrogel in the presence of papain and dextranase, two enzymes known to hydrolyze the respective polymers. The resulting degradation was due to the structure of the co-polymer, not just the presence of the enzymes.

PEG/alpha-hydroxy acids (i.e., polylactic acid [PLA] or polyglycolic acid [PGA]) have a degradation time by hydrolysis which varies from less than 1 day to up to 4 months.

Polysaccharide Hydrogels

Hydrogels made from polysaccharides, naturally hydrophilic substances, are attractive biomaterials because they are less likely to cause the adverse reactions observed with synthetic polymers. Several polysaccharides have been identified in the literature for their use in drug delivery.

Dextran-Based Hydrogels

Dextran is a D-glucose polysaccharide which is produced commercially by *Leuconostoc mesenteroides* bacteria. As shown in FIG. 1, the structure of dextran consists of a central ring containing hydroxyl functional groups which can be used for chemical derivatization. Synovial fluid is a dialysate derived from blood plasma. As a material, it has an egg-white consistency and has non-Newtonian characteristics: its viscosity decreases with increasing shear rate. Normal synovial joints contain about 0.13 to 3.5 ml of synovial fluid. Joint disease can cause the volume of synovial fluid to increase up to 200 ml.

Dipalmitoyl phosphatidylcholine (DPPC) is a phospholipid which has a polar head group and hydrophobic fatty acid tail. Phosphatidylcholine contains a glycerol backbone, two fatty acid chains, and a phosphorylated alcohol (choline). In the dipalmitoyl structure, the fatty acid portion consists of saturated C16 hydrocarbon chains. The concentration and content of synovial fluid changes in diseased joints. In particular, the volume and lipid concentration of synovial fluid in osteoarthritic (OA) and rheumatoid arthritic (RA) joints can increase significantly over normal joints.

Synovial Fluid

Synovial fluid performs several tasks in the synovial joint. For example, it is the source of nutrients for the articular cartilage. It carries metabolic substances to the chondrocytes and provides the waste removal from these cells. Because synovial fluid fills the joint space, it provides hydration to the tissues in the joint. Synovial fluid also functions in lubrication, load bearing, and shock absorption within the joint. The rheological properties of synovial fluid are responsible for optimum joint lubrication.

Synovial fluid may act as a shock absorber, particularly under high loads when the inherent molecules undergo conformational changes. The energy of conformation is stored and released later. In contrast, the molecules serve as lubricants at low loads because they are flexible enough to maintain their conformation.

Diseased Synovial Fluid

Diseased synovial fluid has decreased rheological properties and therefore does not fulfill its normal functions of lubrication and shock absorption. Normal synovial fluid behaves in a non-Newtonian manner: viscosity decreases as shear rate increases. In diseased joints, the synovial fluid's overall viscosity is lowered and it does not display the non-Newtonian behavior. Thus, in one aspect of this invention, an artificial synovial fluid composition is proposed which can provide a viscoelastic or visco-supplementation to a diseased synovial joint. This provides necessary lubrication and may relieve pain.

Synthetic Synovial Fluid

The degeneration or absence of synovial fluid for patients with joint diseases or artificial joints affects their mobility. These patients benefit from a synthetic material which can mimic synovial fluid properties. Particularly, the compositions of this invention do not cause an adverse tissue reaction, and yet contain components naturally found in synovial fluid. Also, the compositions of this invention have a viscosity compatible with natural synovial fluid, and provide similar frictional properties (i.e., lubrication) as the natural materials.

The body does not have a natural enzyme which degrades dextran. Therefore, it has been surprisingly discovered that by using dextran-based hydrogels, one may effectively increase the length of time a hydrogel made from dextran remains intact. In addition, the polysaccharide-based gel of this invention advantageously does not require additional surgeries to remove the material.

Phospholipids are responsible for the lubricating properties of synovial fluid. Phospholipids are the most abundant molecules used as surfactants by the body, they enhance boundary lubrication properties. Also, they are involved in the lubrication and protection of synovial articular cartilage. Further, DPPC phospholipids are particularly useful in the compositions of this invention for incorporation into the polysaccharide hydrogel.

Procedure to Make Dextran-Based Hydrogels

1. Synthesize the Dextran:
Operating conditions:
Nitrogen atmosphere
Room temperature
Stir for 48 hours Ingredients:
25 grams dextran [40,000 m wt: Sigma #D-1662]
225 mL of dimethyl sulfoxide (DMSO) [Aldrich #27,685-5]
5 grams 4 (N, $N^1$-dimethylamino) pyridine (i.e. "DMAP") [Sigma #D-5640]; amount of glycidyl methacrylate [Sigma #M-1157] depends on desired degree of substitution.
For DS-14 (14 percent molar ratio GMA: dextran) add 3.1 mL glycidyl methacrylate;
For DS-28 (28 percent molar ratio glycidyl methacrylate: dextran): add 6.1 mL glycidyl methacrylate.
Then, stop the reaction with 37% hydrochloric acid based on the molar ration of HCl to DMAP:

Operating Conditions:
Room temperature
Ambient atmosphere
Stir for 5 minutes

Ingredients:
Add 3.4 mL HCl to each flask.

Separation of the Dex-Glycidyl Methacrylate from DMSO:
Transfer the thickened solutions to 4-5 dialysis tubes (Sigma #250-7U); place the 2-3 dialysis tubes in 1 L beakers filled with deionized water; keep the DS-14 and DS-28 dialysis tubes in separate beakers; cover the beakers with Parafilm7 to minimize DMSO odors.

Operating Conditions:
Temperature=4° C.
Ambient atmosphere.
Dialyze for 14 days; change the de-mineralized water at least 4 times; freeze-drying the dex-GMA: Transfer the 4-5 dialysis tube contents to nine 50-mL centrifuge tubes; place the capped centrifuge tubes in 20° C. freezer for 24 hours; uncap the centrifuge tubes and put them in lyophilizer containers to freeze-dry for up to 72 hours; keep the DS-14 and DS-28 centrifuge tubes in separate containers. Then, re-cap the centrifuge tubes containing the freeze-dried fluffy product and store them in 20° C. freezer until use.

2. Preparing the Hydrogels:
Make aqueous solutions:
500 mL of a 0.2M phosphate buffer solution (pH=8.5) from $Na_2HPO_4$ (m wt 141.96);
14.2 grams $Na_2HPO_4$ powder; 500 mL deionized water; Adjust the pH with 1M HCl or NaOH; 50 mL of 0.11M ammonium persulfate (APS) solution:
1.255 grams APS [Aldrich #24,861-4]; 50 mL of phosphate buffer from above 50 mL of 0.067 M (N,N,N,N=) Btetramethylethylenediamine (TEMED); 0.5055 mL TEMED [Sigma #T-8133]; 50 mL of phosphate buffer from above.
Prepare a paste of dipalmitoyl phosphatidylcholine lipid (DPPC): [Sigma #P-0763] and phosphate buffer (pH=8.5); put 1 gram DPPC in 20 mL vial; add phosphate buffer (pH=8.5) dropwise; stir with a spatula until the mixture has a toothpaste-like consistency.

Non-Sterile Technique for Hydrogel Formation:

Without Lipids—makes a 1.2 mL hydrogel (approximately); weigh 100 milligrams dex-GMA; add 1 mL phosphate buffer; add 100 μL APS solution; add 100 μL TEMED solution; swirl container to mix contents then set container on level surface or draw solution into a syringe; hydrogel will form in approximately 30 minutes at room temperature.

With Lipids—makes 1.5 mL hydrogel (approximately); weigh 100 milligrams dex-GMA.
Measure a 0.36 mg (rice grain-size) of dipalmitoyl phosphatidylcholine lipid (DPPC) [Sigma #P-0763]/phosphate buffer paste made in step 2b above; add 1 mL phosphate buffer; shake container to suspend lipids in phosphate buffer; add 200 μL APS solution; add 200 μL TEMED solution; swirl container to mix contents swirl container to mix contents then set container on level surface or draw solution into a syringe; hydrogel will form in approximately 30 minutes at room temperature.

Sterile Technique for Hydroqel Formation:

Without Lipids—makes a 1.2 mL hydrogel (approximately); weigh 100 milligrams dex-GMA
Add 2 mL phosphate buffer; syringe filter this dex-GMA/phosphate buffer solution into one well of a 6-well culture plate using a 0.45 micron filter (Pall-Gelman Supor Acrodisc®); syringe filter the APS solution into one well of a 6-well culture plate using a 0.2 micron filter (Pall-Gelman Supor Acrodisc®); syringe filter the TEMED solution into one well of a 6-well culture plate using a 0.2 micron filter (Pall-Gelman Supor Acrodisc®); add 100 μL of the filtered APS solution to the phosphate/dex-GMA mixture; add 100 μL filtered TEMED solution to the phosphate/dex-GMA mixture; swirl container to mix contents then set container on level surface or draw solution into a syringe; hydrogel will form in approximately 30 minutes at room temperature;

with Lipids—makes a 1.5 mL hydrogel (approximately).
Weigh 100 milligrams dex-GMA; measure approximately 0.36 mg (rice grain-size) of dipalmitoyl phosphatidylcholine lipid (DPPC) [Sigma #P-0763]/phosphate buffer paste made in step 2b above
Add 1 mL phosphate buffer; shake container to suspend lipids in phosphate buffer; syringe filter this dex-GMA/phosphate buffer solution into one well of a 6-well culture plate using a 0.45 micron filter (Pall-Gelman Supor Acrodisc7); syringe filter the APS solution into one well of a 6-well culture plate using a 0.2 micron filter (Pall-Gelman Supor Acrodisc7); syringe filter the TEMED solution into one well of a 6-well culture plate using a 0.2 micron filter (Pall-Gelman Supor Acrodisc7); add 200 μL of the filtered APS solution to the phosphate/dex-GMA mixture; swirl container to mix contents then set container on level surface or draw solution into a syringe; hydrogel will form in approximately 30 minutes at room temperature.

EXAMPLE

Synovial fluid can be reconstituted based on an adapted technique. Five solutions (pH=7) containing a fixed amount of high purity hyaluronic acid (Genzyme Corporation, Cambridge, Mass.) ($1.7 \times 10^6$ Daltons, 2.84 mg/ml or 0.287%) dissolved in aqueous sodium chloride solution (0.85% (w/v)) containing 0.05% sodium azide were made to contain physiologically significant amounts of DPPC (0.0, 0.025, 0.2 (normal), 0.4, (osteoarthritis (OA)), 0.8 (rheumatoid arthritis (RA) mg/ml). Phospholipid concentrations were verified using a phosphate assay against a set of standards in a UV/VIS spectrophotometer (Model 219 Cary, Varian Associates, Sunnyvale, Calif.). The viscosity of each solution was measured using a cup and bob rheometer (Epprecht-Contraves Rheomat 15T, Mettler Corp., Cincinnati, Ohio). Viscosity measurements were taken at various shear rates, while the temperature was held constant at 23° C.

It is possible to evaluate the ability of dipalmitoyl phosphatidylcholine (DPPC) to lower the coefficient of friction ($\mu$) between rigid bearings when acting as a boundary lubricant at stresses in the range experienced by weight-bearing joints (3.5, 4.5, and 5.5 MPa). Friction tests were conducted in a fluid environment simulating different stage of synovial degeneration using the solutions previously described for the rheological analysis. A specially designed pin-on-plate friction table was used for friction testing. Two glass cylindrical pins (1 cm×2.5 cm) were fastened to a small steel plate upon which weights were placed to apply equal loading to each of the nominal line contacts on a flat glass plate. The arrangement of the pins allowed the upper surface to be self-supported and thus avoiding the interference of mechanical constraints on the friction force measurements.

Strain gages were mounted on the upper surface to provide a friction force transducer. The output from the strain gages were amplified, then collected and calibrated using an analog-to-digital converter (National Instruments) and a personal Macintosh IIsi computer with a data analysis software package (LabView II by National Instruments). The raw signal was filtered to remove vibrations not related to friction. The signals from the friction force transducers are compared before and after filtering. Borosilicate glass (Pyrex™) was used as the non-deformable bearing materials for friction studies. Since Pyrex™ has an elastic modulus of 62.7 GPa and poisson's ratio of 0.2, effects of hysteresis friction are negligible.

Phosphatidylcholine, which is the backbone of the phospholipid structure, has been shown to orient in organized bilayers on this material. Using a stroke of 75 mm and a frequency of 0.2 Hz, a maximum entraining velocity of 30 mm/sec which is the minimum speed range required for fluid film lubrication, the static and dynamic coefficient of friction were measured for each sinusoidal cycle for 5 minutes for 0, 100, 1000, 2000, and 3000 cycles. From the transient friction force measurements, the coefficient of friction at the point of maximum entrainment velocity was calculated for each experiment. Non-contact profilometry with a 20× Linnik magnification head was used to observe a roughness average of 2.27-0.58 nm (Peak-to-Valley of 19.65-7.09 nm) for the glass rods and plates (Topo-3D™ by Wyko, Corp., Tuscon, Ariz.).

Five experiments were conducted for each loading condition. After testing, the topography of the surfaces were examined with scanning electron microsocopy and non-contact profilometry. A phosphate assay was also performed to evaluate the transfer of DPPC from the solution onto the glass surface. A statistical general linear model (GLM) was used to analyze the effect of DPPC concentration and loading on the coefficients of friction.

The results revealed that the viscosity of reconstituted synovial fluid is significantly dependent on the concentration of phospholipid. However, the depletion of lipid in the solution did not change the thixotropic behavior of the fluid and its non-newtonian character as a function of shear rate. Results from the friction study indicate that the presence of phospholipid in synthetic synovial fluid significantly decreases the coefficient of friction between rigid bearings. It appears that the conditions used did not provide for the formation of a fluid film between the bearings and that a transfer of DPPC molecules onto the glass bearings protective layer. The concentration, however, had no effect on the coefficient of friction; indicating that the amount of phospholipid does not influence the effectiveness of lubrication under conditions favorable to hydrodynamic and boundary lubrication. Boundary lubrication contributes significantly to the protection of bearing surfaces in adverse conditions which do not permit fluid film lubrication.

Thus, it has been shown that DPPC can effectively protect surfaces and reduce the coefficient of friction between glass surfaces. This study also shown that DPPC is effective in protecting the surface against wear. Boundary lubrication is an effective method to protect total joint replacement surfaces providing that they can attract a boundary surfactant.

Hydroxyl groups on the dextran chain are acryloylated (i.e., activated) using the glycidyl methacrylate ("GM"). In general, a rheometer is used to measure flow properties of fluids. One of these properties is viscosity. The units for viscosity are Pascal (seconds).

One advantage of using dextran in the compositions of the invention is that it will be slowly broken down. In arthritic human joints, there usually is a significant amount of hyaluronidase that will considerably speed up the degradation of hyaluronic acid. Therefore, lipid molecules can be released with time to replenish the surfaces of the joint.

It is understood by one of ordinary skill in the art that the present discussion is a description of exemplary embodiments only, and is not intended as limiting the broader aspects of the present invention, which broader aspects are embodied in the exemplary constructions. The invention is shown by example in the appended claims.

What is claimed is:

1. A method comprising providing to a joint an effective amount of a composition comprising:
   (a) one or more lipids, and
   (b) a dextran-based hydrogel carrier, wherein the one or more lipids are entrapped within the dextran-based hydrogel carrier for delivery of the one or more lipids to the joint.

2. The method of claim 1 in which the joint is a natural joint.

3. The method of claim 1 in which the joint is an artificial joint.

4. The method of claim 1 in which the joint is a knee joint.

5. The method of claim 1 in which the composition is provided to the joint following a surgical procedure on the joint.

6. The method of claim 1 in which the composition is provided to an artificial joint in vitro to simulate wear performance of the joint.

7. The method of claim 1 wherein the one or more lipids are selected from a group of phospholipids consisting of phosphatidylcholine, phosphatidylethanolamine, phosphatidylserine, phosphatidylglycerol, phosphatidylinositol, sphingomyelin alpha-dipalmitoyl phosphatidylcholine (alpha-DPPC), and mixtures thereof.

8. A method for treating joint disorder which comprises injecting into a joint a composition comprising:
   (a) a dextran-based hydrogel carrier, and
   (b) one or more phospholipids entrapped within the dextran-based hydrogel for delivery to the joint.

9. The method of claim 8 in which the composition is employed as a viscosity supplement for natural synovial fluid in the joint.

10. The method of claim 1, wherein the method is an in vivo visco-supplementation method.

11. The method of claim 5, wherein the surgical procedure is a total joint replacement procedure.

12. The method of claim 1, wherein the dextran-based hydrogel is a dextran/glycidyl methacrylate copolymer hydrogel.

13. The method of claim 1, wherein the composition is a biocompatible composition.

14. The method of claim 1, wherein the dextran-based hydrogel is a biodegradable hydrogel, the method further comprising injecting the composition into the joint in vivo.

15. The method of claim 8, wherein the dextran-based hydrogel carrier is a biodegradable dextran/glycidyl methacrylate copolymer hydrogel.

16. The method of claim 8 the method further comprising
   degrading the dextran-based hydrogel;
   releasing the one or more phospholipids into the joint; and
   incorporating the phospholipids into a cartilage surfactant layer in the joint.

* * * * *